United States Patent
El A'mma et al.

(10) Patent No.: US 7,083,801 B2
(45) Date of Patent: Aug. 1, 2006

(54) STABILIZED HALOALKYNYL MICROBICIDE COMPOSITIONS

(75) Inventors: Beverly Jean El A'mma, Perkiomenville, PA (US); Susan Lynn Nagahashi, Warminster, PA (US)

(73) Assignee: Rohm and Haas Company

( * ) Notice: Subject to any disclaimer, the term of this patent is extended or adjusted under 35 U.S.C. 154(b) by 149 days.

(21) Appl. No.: 10/602,992

(22) Filed: Jun. 24, 2003

(65) Prior Publication Data
US 2004/0014736 A1  Jan. 22, 2004

Related U.S. Application Data

(60) Provisional application No. 60/396,676, filed on Jul. 18, 2002.

(51) Int. Cl.
*A01N 25/02* (2006.01)
*A01N 29/04* (2006.01)
*A01N 29/10* (2006.01)

(52) U.S. Cl. .................. 424/405; 424/78.09; 523/122; 514/372; 514/422; 514/479

(58) Field of Classification Search ................ 514/372, 514/422, 479; 424/78.09, 405; 523/122
See application file for complete search history.

(56) References Cited

U.S. PATENT DOCUMENTS

| 5,292,763 A | * | 3/1994 | Hsu | 514/372 |
| 5,591,760 A | | 1/1997 | Hsu | 514/372 |
| 5,916,930 A | | 6/1999 | Gaglani et al. | 523/122 |
| 5,955,483 A | | 9/1999 | Gaglani et al. | 514/357 |
| 2003/0199490 A1 | | 10/2003 | Antoni-Zimmerman et al. | |

FOREIGN PATENT DOCUMENTS

WO  WO 09/22543  5/1998

* cited by examiner

*Primary Examiner*—Christopher S. F. Low
*Assistant Examiner*—C. Delacroix-Muirheid
(74) *Attorney, Agent, or Firm*—Thomas Rogerson

(57) ABSTRACT

Antimicrobial compositions based on haloalkynyl active ingredients that are chemically stable in the presence of chelated metal ion are disclosed. Particularly preferred is the use of metal ion chelating agents based on selected amine compounds that provide the metal ion in a form sufficient to provide stability to other antimicrobial components in the aqueous composition, but without concurrently degrading the antimicrobial effectiveness of the haloalkynyl active ingredient.

9 Claims, No Drawings

STABILIZED HALOALKYNYL MICROBICIDE COMPOSITIONS

CROSS REFERENCE TO RELATED PATENT APPLICATION

This is a non-provisional application of prior pending U.S. provisional application Ser. No. 60/396,676 filed Jul. 18, 2002.

BACKGROUND

This invention relates to aqueous compositions containing haloalkynyl microbicide in the presence of metal ions. In particular, the invention is directed to stabilized compositions of halopropargyl microbicides where the metal ions are provided in the form of chelated metal ion. Typically the aqueous compositions contain additional microbicidal compounds, such as 3-isothiazolones, and are useful in various end use applications, such as in the preservation of paints against contamination by microorganisms.

Various types of coatings are used to protect substrates, particularly wood, against both physical and microbial degradation. These coatings, typically in the form of paints, lacquers and varnishes, function as carriers for microbicidal agents and also provide a protective barrier against the environment. Of particular use are aqueous-based coatings, such as latex paints.

A well-known class of microbicides used in coating compositions are those based on haloalkynyl compounds, in particular halopropargyl compounds, and especially compounds containing an iodopropargyl group, such as 3-iodo-2-propynylbutylcarbamate (IPBC). Haloalkynyl compounds, including halo-propargyl carbamates, are formulated with a variety of other ingredients in both aqueous and organic solvent mixtures to form coating materials. Often additional antimicrobial agents are included in the formulations to enhance the overall efficacy of the microbicidal activity. For example, when 3-isothiazolones, such as 4,5-dichloro-2-n-octyl-3-isothiazolone, are included in the aqueous coating composition, it is desirable to include metal ion stabilizers to prolong the activity of the 3-isothiazolone component. However, metal ions are known to chemically degrade haloalkynyl microbicides and detract from the overall antimicrobial effectiveness of the formulation. For example, U.S. Pat. No. 5,916,930 discloses the use of a wide range of chelating agents as additives to alkyd compositions containing un-chelated transition metal ions and haloalkynyl compounds.

There is a need for stabilized aqueous compositions that provide the enhanced activity of antimicrobial agents, such as haloalkynyl microbicides, while at the same time tolerating the presence of metal ions, which otherwise would degrade the haloalkynyl active ingredient. The problem addressed by the present invention is to overcome stability deficiencies of antimicrobial formulations containing haloalkynyl microbicides in the presence of metal ions by providing aqueous compositions of haloalkynyl compounds in the presence of chelated metal ion.

STATEMENT OF INVENTION

The present invention provides a microbicidal composition comprising (a) 0.5 to 20 percent, based on weight of the composition, of haloalkynyl compound; (b) 0.3 to 10 percent, based on weight of the composition, of chelated metal ion compound; (c) 40 to 99 percent, based on weight of the composition, of water; and (d) zero up to 30 percent, based on weight of the composition, of 3-isothiazolone compound.

The present invention further provides a method of inhibiting the growth of microorganisms in a locus comprising introducing to, at or on, the locus a microorganism inhibiting amount of the aforementioned microbicidal composition.

In another embodiment the present invention provides a microbicidal composition comprising (a) 5 to 10 percent, based on weight of the composition, of haloalkynyl compound selected from one or more of 3-iodo-2-propynylpropylcarbamate, 3-iodo-2-propynylbutylcarbamate, 3-iodo-2-propynyl-hexylcarbamate, 3-iodo-2-propynylcyclohexylcarbamate and 3-iodo-2-propynyl-phenylcarbamate; (b) 2 to 5 percent, based on weight of the composition, of chelated metal ion compound, wherein the chelated metal ion compound is a 1:1 molar complex of amine chelating agent and copper ion and the amine chelating agent is selected from one or more of ethylenediaminetetraacetic acid and salts thereof, 1,3-diaminopropanetetraacetic acid and salts thereof, 1,2-propylenediaminetetraacetic acid and salts thereof, 1,2-diaminocyclohexanetetraacetic acid and salts thereof, and ethylenediamine; (c) 60 to 70 percent, based on weight of the composition, of water; (d) 10 to 20 percent, based on weight of the composition, of 3-isothiazolone compound selected from one or more of 2-n-octyl-3-isothiazolone, 4,5-dichloro-2-n-octyl-3-isothiazolone, benzisothiazolone and N-alkyl derivatives of benzisothiazolone; and (e) zero up to 20 percent, based on weight of the composition, of adjuvants, selected from one or more of surfactants, dispersants and co-solvents.

DETAILED DESCRIPTION

We have discovered that haloalkynyl compounds may be combined with selected chelated metal ions to provide aqueous compositions having effective antimicrobial activity and prolonged stability of the haloalkynyl active ingredient, whereas the metal ion component in un-chelated form would otherwise degrade the haloalkynyl compound in aqueous compositions.

It has been discovered that selected chelating (sequestering) agents provide the metal ion in a form sufficient for the metal ion to provide stability to other antimicrobial components in the aqueous composition, but without concurrently degrading the antimicrobial effectiveness of haloalkynyl active ingredient. In another aspect, the present invention involves a method of stabilizing antimicrobial activity of an aqueous composition containing a haloalkynyl compound and a metal ion comprising providing the metal ion in the form of a chelated metal ion compound.

As used herein, the following terms have the designated definitions, unless the context clearly indicates otherwise. The term "microbicide" or "antimicrobial" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter. Unless otherwise specified, ranges listed are to be read as inclusive and combinable, temperatures are in degrees centigrade (°C), and references to percentages (%) are by weight.

The aqueous microbicidal compositions of the present invention typically comprise 0.5 to 20%, preferably 2 to 15% and more preferably 5 to 10%, of haloalkynyl compound; 0.3 to 10%, preferably 0.5 to 7% and more preferably 2 to 5%, of chelated metal ion compound; 40 to 99%, preferably 50 to 90% and more preferably 60 to 70%, of water; and zero up to 30%, preferably 1 to 25% and more preferably 5 to 20%, of 3-isothiazolone compound. Optionally, zero up to 20%, typically 5 to 15%, of adjuvant materials may be added to the aqueous composition, such as, for example surfactants, binders, dispersants, thickeners, anti-freeze agents, colorants, pigments, co-solvents, stabilizers, other antimicrobial agents, scale inhibitors and anti-corrosion additives; typically the adjuvants are selected from one or more of surfactants, dispersants and co-solvents.

Suitable haloalkynyl compounds useful in the compositions of the present invention include those of formula (I):

where Y is halogen (chlorine, bromine, iodine, fluorine), a is an integer from 1 to 3, and X is an organic functional group attached, via an oxygen, nitrogen, sulfur or a carbon atom, to an adjacent methylene (—CH$_2$—) group. Suitable functional groups representing the X substituent in formula (I) include, for example, ether, ester, carbamate, amine, amide, urea, nitrile, thiol, thiane, sulfone, sulfoxide and alkyl groups.

Preferably the haloalkynyl compounds are halopropargyl (halopropynyl) derivatives, particularly the fungicidally active iodopropargyl derivatives. Representative halopropargyl compounds include, for example, iodopropargyl alcohol derivatives, such as the esters, ethers, acetals, carbamates and carbonates; and iodopropargyl derivatives of pyrimidines, thiazolinones, tetrazoles, triazinones, sulfamides, benzothiazoles, ammonium salts, carboxamides, hydroxamates and ureas.

Particularly preferred among these compounds are the haloalkynyl carbamates as represented by formula (II):

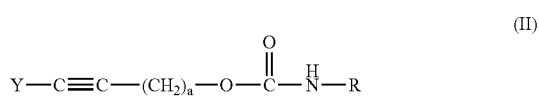

where Y is halogen (chlorine, bromine, iodine, fluorine), a is an integer from 1 to 3, and R is hydrogen, a substituted or unsubstituted alkyl group having 1 to 20 carbon atoms, a substituted or unsubstituted aryl, alkylaryl or aralkyl group having 6 to 20 carbon atoms, or a substituted or unsubstituted cycloalkyl or cycloalkenyl group having 3 to 10 carbon atoms. Suitable R substituents include, for example, methyl, ethyl, propyl, n-butyl, t-butyl, pentyl, hexyl, heptyl, octyl, nonyl, decyl, dodecyl and octadecyl, cyclohexyl, phenyl, benzyl, tolyl, cumyl, halogenated alkyl and aryl groups (chlorobutyl, chlorophenyl), and alkoxy aryl groups (ethoxyphenyl).

Especially preferred are iodopropargyl (also known as iodopropynyl) carbamates corresponding to formula (II), where Y is iodine, a is 1 and R is a (C$_3$–C$_6$)alkyl, cycloalkyl or phenyl group. Suitable iodopropargyl carbamates useful in the compositions of the present invention include, for example, 3-iodo-2-propynylpropylcarbamate, 3-iodo-2-propynylbutylcarbamate (IPBC), 3-iodo-2-propynylhexylcarbamate, 3-iodo-2-propynylcyclohexylcarbamate and 3-iodo-2-propynylphenylcarbamate; most preferred is 3-iodo-2-propynylbutylcarbamate or 3-iodo-2-propargylbutylcarbamate (IPBC)

Suitable chelated metal ion compounds useful in the compositions of the present invention comprise metal ion selected from one or more of copper, zinc, ferric, magnesium, cobalt and silver ions; preferably the metal ion is copper ion.

Suitable chelated metal ion compounds useful in the compositions of the present invention comprise metal ion chelated with one or more amine chelating agents selected from the group consisting of alkylenepolyamines and carboxylate-containing amine compounds.

Preferably the chelated metal ion compounds useful in the present invention are those wherein the chelated metal compound is in the form of a 1:1 molar complex of amine chelating agent and the metal ion, preferably copper ion. By a 1:1 molar complex, it is understood that the molar ratio of the amine chelating agent to the metal ion is 1:1. However, other molar ratios (such as 2:1 or 3:1, in whole number integers) of chelating agent to metal ion may also be suitable for use in the present invention, depending on the particular chelating agent/metal ion combination based on the number of binding sites available per chelating agent molecule and valence of the metal ion. For example, ethylenediamine (EDA) may form 1:1, 2:1 or 3:1 molar ratio complexes with copper ion.

Suitable amine chelating agents useful in the compositions of the present invention include those selected from the group consisting of alkylenepolyamines and carboxylate-containing amine compounds; preferably the carboxylate-containing amine compound is a carboxylate-containing alkylenepolyamine compound. Suitable alkylenepolyamines include, for example, ethylenediamine (EDA), propylenediamine (1,2-diaminopropane), diethylenetriamine and triethyl-enetetraamine. Suitable carboxylate-containing amine and alkylenepolyamine compounds include, for example, ethylenediaminetetraacetic acid (EDTA) and salts thereof, hydroxyethylenediaminetetraacetic acid and salts thereof, ethylenediaminedisuccinic acid (EDDS) and salts thereof, iminodisuccinic acid and salts thereof, nitrilotriacetic acid and salts thereof, 1,3-diaminopropanetetra-acetic acid and salts thereof, 1,2-diaminocyclohexanetetraacetic acid and salts thereof, 1,2-propylenediaminetetraacetic acid and salts thereof. Preferably, the amine chelating agent is selected from one or more of ethylenediaminetetraacetic acid and salts thereof, 1,3-diaminopropanetetraacetic acid and salts thereof, 1,2-propylenediaminetetraacetic acid and salts thereof, 1,2-diaminocyclohexane-tetraacetic acid and salts thereof, and ethylenediamine.

Whereas the types of polyamine chelating agents described above are suitable for use in the compositions of the present invention, I have found that not all chelating agents provide sufficient stability to the haloalkynyl active ingredient to allow subsequent effective antimicrobial control. Unexpectedly, I have found that aromatic polyamine chelating agents, and some oxygen-containing chelating agents are ineffective in stabilization against degradation of haloalkynyl active ingredient. For example, see Examples 3-IC through 3-4C (Table 3) where gluconic acid (gluconate), citric acid (citrate), acetoacetonate and 2,2'-dipyridyl (2,2'-bipyridine) chelated copper complexes are shown to be ineffective in stabilization of IPBC in the presence of these forms of complexed copper.

Suitable 3-isothiazolone compounds useful in the compositions of the present invention include, for example, 2-n-octyl-3-isothiazolone, 4,5-dichloro-2-n-octyl-3-isothiazolone, 4,5-dichloro-2-benzyl-3-isothiazolone, 2-cyclohexyl-3-iso-thiazolone, 2-methyl-3-isothiazolone, 5-chloro-2-methyl-3-isothiazolone, 2-benzyl-3-isothiazolone, benzisothiazolone and N-alkyl derivatives of benzisothiazolone. Preferably, the 3-isothiazolone is selected from one or more of 2-n-octyl-3-isothiazolone, 4,5-dichloro-2-n-octyl-3-isothiazolone, benzisothiazolone and N-alkyl derivatives of benzisothiazolone.

When used, optional adjuvant materials comprise up to 20% of the aqueous composition. Representative adjuvant materials added to the compositions include, for example, surfactants, dispersants and co-solvents. Suitable surfactants include both nonionic and ionic surfactants, such as anionic surfactants. Suitable co-solvents include, for example, glycols (such as ethylene glycol, propylene glycol, diethylene glycol, dipropylene glycol, tripropylene glycol, polyethylene glycol and polypropylene glycol) and glycol ethers (such as propylene glycol n-butyl ether, propylene glycol tert-butyl ether, propylene glycol methyl ether, dipropyleneglycol methyl ether, tripropylenelene glycol methyl ether and propylene glycol n-butyl ether).

The microbicidal compositions of the present invention can be used to inhibit the growth of microorganisms by introducing a microbicidally effective amount of the compositions onto, into, or at a locus subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the microbicidal compositions of the present invention are used to inhibit the growth of microorganisms at a locus selected from one or more of emulsions, dispersions, paints, latexes, household products, cosmetics, toiletries, shampoos, soaps, detergents and industrial cleaners. In particular, the microbicidal compositions are useful in coating formulations, such as emulsions, dispersions, paints and latexes.

The specific amount of the haloalkynyl compositions necessary to inhibit or control the growth of microorganisms in a locus depends upon the level and type of haloalkynyl compound, the presence of any additional antimicrobial agents, and the particular locus to be protected. Typically, the amount of the microbicidal compositions of the present invention to control the growth of microorganisms in a locus is sufficient if it provides from 0.1 to 10,000 ppm total antimicrobial active ingredient in the locus. It is preferred that the total active ingredient be present in an amount of 1 to 5000 ppm, and more preferably from 10 to 3000 ppm, in the locus.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions:

| | | |
|---|---|---|
| DCOIT | = | 4,5-Dichloro-2-n-octyl-3-isothiazolone |
| DBSA | = | Dodecylbenzenesulfonic acid |
| IPBC | = | 3-Iodo-2-propynylbutylcarbamate |
| EDTA | = | Ethylenediaminetetraacetic acid, disodium salt |
| HEDTA | = | Hydroxyethylenediaminetetraacetic acid, disodium salt |
| DAPTA | = | 1,3-Diaminopropanetetraacetic acid, disodium salt |
| DACHTA | = | 1,2-Diaminocyclohexanetetraacetic acid, disodium salt |
| DPTA | = | 1,2-Propylenediaminetetraacetic acid, disodium salt |
| EDA | = | Ethylenediamine |

EXAMPLE 1

Preparation of Chelated Copper Compounds

Chelated metal compounds were prepared as follows, using the copper EDTA complex as a representative example; in each case, 1:1 molar complexes were prepared. Copper chloride (10.0 g of $CuCl_2.2H_2O$, FW=170.5), 0.06 mole, was dissolved into 100 mL deionized water. While stirring, the chelating agent (free acid form or sodium salt), 0.06 mole (17.4 g of EDTA), was added to the copper chloride solution. The pH of the mixture was adjusted to >9 with NaOH and the mixture was then stirred for one hour. The mixture was then transferred to a crystallizing dish and heated to 100° C. for 12–16 hours to evaporate the water. The solid residue was recovered and pulverized with a mortar and pestle to provide the chelated metal compound as a dry powder.

EXAMPLE 2

Table 1 summarizes the effect of some copper salts on the stabilility of IPBC in an aqeuous concentrate formulation containing 3-isothiazolone. A concentrate solution of 3-isothiazolone (12.3–13.6% DCOIT), haloalkynyl compound (5.9–6.6% IPBC), surfactants (1–2%), co-solvent (10% dipropylene glycol/tripropylene glycol), pigment (1% titanium dioxide) and thickeners/dispersants (1–2%) in water (approximately 65%) was prepared and stored for up to 4 weeks at elevated temperature (40° C.) in both the absence of copper ion and in the presence of copper ion (in the form of two different copper salts). Whereas DCOIT was stable under these conditions, the copper ion (conventional stabilizer for DCOIT) totally degraded the IPBC component of the mixture. The amount of copper (as cupric ion) used in these experiments corresponded to 0.5–0.6% by weight of the mixture. Values of "% DCOIT or % IPBC remaining" in Tables 1–3 that are greater than 100% are considered to represent 100% retention of active ingredient (within experimental error of analytical measurement).

TABLE 1

| Metal Salt | Weeks Stored at 40° C. | % DCOIT Remaining | % IPBC Remaining |
|---|---|---|---|
| None | 0 | 100 | 100 |
| | 2 | 92 | 97 |
| | 4 | 101 | 98 |
| 3% Cu(DBSA)$_2$ | 0 | 100 | 100 |
| | 2 | 102 | 0 |
| 1.8% Cu(NO$_3$)$_2$ | 0 | 100 | 100 |
| | 4 | 103 | 0 |

EXAMPLE 3

Table 2 summarizes the effect of chelated metal ion (EDTA complex) versus un-chelated metal ion (nitrate and DBSA salts) on the stabililiy of IPBC in a concentrate formulation containing 3-isothiazolone. The same concentrate solution of DCOIT/IPBC described in Example 2 was used. In both cases involving un-chelated metal ion (comparatives 2-1C and 2-4C), the IPBC was totally degraded after 4 weeks at 40° C. When chelating agent was added to a mixture of IPBC/DCOIT and copper nitrate (comparative 2-5C), approximately 80% of the IPBC was degraded over the same time period, thus demonstrating that the metal ion should be in the chelated form before being contacted with the IPBC. Satisfactory IPBC stability (at least 80% retention after 4 weeks) was maintained only when metal ion already in chelated form (2-2 and 2-3) was used as the DCOIT stabilizer. The amount of copper (as cupric ion) used in these experiments corresponded to about 0.5% by weight of the mixture for 2-1C and 2-2, 0.6% for 2-4C and 2-5C and approximately 1.2% for 2-3.

TABLE 2

| Metal Salt | Ex # | Weeks Stored at 40° C. | % DCOIT Remaining | % IPBC Remaining |
| --- | --- | --- | --- | --- |
| 3% Cu(DBSA)$_2$ | 2-1C | 0 | 100 | 100 |
| | | 4 | 81 | 0 |
| 3% Cu(EDTA) | 2-2 | 0 | 100 | 100 |
| | | 4 | 96 | 96 |
| 7.2% Cu(EDTA) | 2-3 | 0 | 100 | 100 |
| | | 4 | 104 | 105 |
| 1.8% Cu(NO$_3$)$_2$ | 2-4C | 0 | 100 | 100 |
| | | 4 | 111 | 0 |
| 1.8% Cu(NO$_3$)$_2$ + 4% EDTA* | 2-5C | 0 | 100 | 100 |
| | | 4 | 96 | 21 |

*EDTA added immediately after copper nitrate was added to IPBC/DCOIT mixture

EXAMPLE 4

Table 3 provides a comparison of additional chelated metal ion compounds (3-5 through 3-9) useful in the present invention versus chelated metal ion compounds (comparatives 3-1C through 3-4C) involving chelating agents other than the alkylenepolyamine and carboxylate-containing amine chelating compounds required by the present invention; the latter group provided unsatisfactoy IPBC stability. Stability studies were performed similarly to those described in Examples 2 and 3. The amount of copper (as cupric ion) used in these experiments corresponded to about 0.5% by weight of the mixture.

TABLE 3

| Metal Salt | Ex # | Weeks Stored at 40° C. | % DCOIT Remaining | % IPBC Remaining |
| --- | --- | --- | --- | --- |
| Copper(citrate) | 3-1C | 0 | 100 | 100 |
| | | 4 | 97 | 56 |
| Copper(acetoacetonate) | 3-2C | 0 | 100 | 100 |
| | | 4 | 91 | 5 |
| Copper(D-gluconate) | 3-3C | 0 | 100 | 100 |
| | | 4 | 90 | 0 |
| Copper(2,2'-dipyridyl) | 3-4C | 0 | 100 | 100 |
| | | 4 | 125 | 0 |
| Copper(EDA) | 3-5 | 0 | 100 | 100 |
| | | 4 | 92 | 100 |
| Copper(HEDTA) | 3-6 | 0 | 100 | 100 |
| | | 4 | 80 | 87 |
| Copper(DAPTA) | 3-7 | 0 | 100 | 100 |
| | | 4 | 91 | 93 |
| Copper(DACHTA) | 3-8 | 0 | 100 | 100 |
| | | 4 | 94 | 96 |
| Copper(DPTA) | 3-9 | 0 | 100 | 100 |
| | | 4 | 106 | 114 |

We claim:

1. A microbicidal composition comprising:
   (a) 0.5 to 20 percent, based on weight of the composition, of one or more haloproparagyl compounds;
   (b) 0.3 to 10 percent, based on weight of the composition, of chelated metal ion compound wherein the chelated metal ion compound comprises a metal ion chelated with one or more amine chelating agents selected from the group consisting of alkylenepolyamines and carboxylate-containing amine compounds;
   (c) 40 to 99 percent, based on weight of the composition, of water; and
   (d) zero up to 30 percent, based on weight of the composition, of 3-isothiazolone compound.

2. The composition of claim 1 wherein the halopropargyl compounds are selected from one or more of the group consisting of 3-iodo-2-propynylpropyl-carbamate, 3-iodo-2-propynylbutylcarbamate, 3-iodo-2-propynylhexylcarbamate, 3-iodo-2-propynylcyclohexylcarbamate and 3-iodo-2-propynylphenylcarbamate.

3. The composition of claim 1 wherein the chelated metal compound comprises metal ion selected from one or more of copper, zinc, ferric, magnesium, cobalt and silver ions.

4. The composition of claim 1, wherein the chelated metal ion compound is in the form of a 1:1 molar complex of amine chelating agent and copper ion.

5. The composition of claim 1 wherein the amine chelating agent is selected from one or more of ethylenediaminetetraacetic acid and salts thereof, hydroxyethylenediaminetetraacetic acid and salts thereof, 1,3-diaminopropanetetraacetic acid and salts thereof, 1,2-diaminocyclohexanetetraacetic acid and salts thereof, 1,2-propylenediaminetetraacetic avid and salts thereof, ethylene-diamine, propylenediamine, diethylenetriamine and triethylenetetrasmine.

6. The composition of claim 1 comprising 1 to 25 percent of 3-isothiazolone compound.

7. The composition of claim 1, wherein the 3-isothiazolone compound is selected from one or more of 2-n-octyl-3-isothiazolone, 4,5-dichloro-2-n-octyl-3-isothiazolone, benzisothiazolone and N-alkyl derivatives of benzisothiazolone.

8. A microbicidal composition comprising:
   (a) 5 to 10 percent, based on weight of the composition, of haloalkynyl compound selected from one or more of 3-iodo-2-propynylpropylcarbamate, 3-iodo-2-propynylbutylcarbamate, 3-iodo-2-propynylhexylcarbamate, 3-iodo-2-propynylcyclohexylcarbamate and 3-iodo-2-propynylhexylcarbamate;
   (b) 2 to 5 percent, based on weight of the composition, of chelated metal ion compound, wherein the chelated metal ion compound is a 1:1 molar complex of amine chelating agent and copper ion and the amine chelating agent is selected from one or more of ethylenediaminetetraacetic acid and salts thereof, 1,3-diaminopropanetetraacetic acid and salts thereof, 1,2-propylenediaminetetraacetic acid and salts thereof, 1,2-diaminocyclohexanetetraacetic acid and salts thereof, and ethylenediamine;
(c) 60 to 70 percent, based on weight of the composition, of water;
(d) 10 to 20 percent, based on weight of the composition, of 3-isothiazolone compound selected from one or more of 2-n-octyl-3-isothiazolone, 4,5-dichloro-2-n-octyl-3-isothiazolone, benzisothiazolone and N-alkyl derivatives of benzisothiazolone; and
(e) zero up to 20 percent, based on weight of the composition, of adjuvants, selected from one or more of surfactants, dispersants and co-solvents.

9. A method of inhibiting the growth of microorganisms in a locus comprising introducing to, at or on, the locus a microorganism inhibiting amount of a microbicidal composition comprising:
(a) 0.5 to 20 percent, based on weight of the composition, of one or more halopropargyl compounds;
(b) 0.3 to 10 percent, based on weight of the composition, of chelated metal ion compound wherein the chelated metal ion compound comprises a metal ion chelated with one or more amine chelating agents selected from the group consisting of alkylenepolyamines and carboxylate-containing amine compounds;
(c) 40 to 99 percent, based on weight of the composition, of water; and
(d) zero up to 30 percent, based on weight of the composition, of 3-isothiazolone compound.

* * * * *